United States Patent
Betournay et al.

(10) Patent No.: US 10,745,339 B2
(45) Date of Patent: Aug. 18, 2020

(54) METHODS FOR PRODUCTION OF BIO-BASED LUBRICANTS AND RELATED FLUIDS

(71) Applicant: STUFFF Lubricants, Inc., Richards Landing (CA)

(72) Inventors: Bill Betournay, Richards Landing (CA); Viktoria McLea, Richards Landing (CA)

(73) Assignee: STUFFF Lubricants, Inc., Richards Landing (CA)

( * ) Notice: Subject to any disclaimer, the term of this patent is extended or adjusted under 35 U.S.C. 154(b) by 150 days.

(21) Appl. No.: 15/267,966

(22) Filed: Sep. 16, 2016

(65) Prior Publication Data

US 2017/0073297 A1    Mar. 16, 2017

(30) Foreign Application Priority Data

Sep. 16, 2015 (CA) .................................... 2904710

(51) Int. Cl.
| | |
|---|---|
| *C07C 67/00* | (2006.01) |
| *C07C 67/03* | (2006.01) |
| *C10M 105/34* | (2006.01) |
| *C07C 67/02* | (2006.01) |
| *C10M 177/00* | (2006.01) |

(52) U.S. Cl.
CPC .............. *C07C 67/03* (2013.01); *C07C 67/02* (2013.01); *C10M 105/34* (2013.01); *C10M 177/00* (2013.01); *C10M 2207/2815* (2013.01); *C10N 2230/64* (2013.01)

(58) Field of Classification Search
CPC ...... C07C 67/03; C07C 67/02; C10M 177/00; C10M 105/34; C10M 2207/2815; C10N 2230/64
See application file for complete search history.

(56) References Cited

U.S. PATENT DOCUMENTS

| | | | |
|---|---|---|---|
| 7,838,474 B2 | 11/2010 | Boffa | |
| 8,304,574 B2 | 11/2012 | Elomari et al. | |
| 8,361,170 B2 | 1/2013 | Martin | |
| 8,367,739 B2 | 2/2013 | Zaki et al. | |
| 8,507,423 B2 | 8/2013 | Elomari et al. | |
| 8,680,029 B2 | 3/2014 | Habeeb et al. | |
| 8,741,822 B2 | 6/2014 | Narine et al. | |
| 8,962,873 B2 | 2/2015 | Summers et al. | |
| 9,090,849 B2 | 7/2015 | Adamczewska et al. | |
| 2009/0320353 A1* | 12/2009 | Reaney ................. | C10L 1/1802 44/306 |
| 2011/0269654 A1* | 11/2011 | Marlin ...................... | C10L 1/02 508/216 |
| 2015/0159109 A1 | 6/2015 | Cholli et al. | |

OTHER PUBLICATIONS

Amit Sarin, Biodiesel: Production and Properties, 2012, pp. 5-23 (Year: 2012).*
Sarin, A. "Biodiesel: Production and Properties", Royal Society of Chemistry, Cambridge 2012, Chapter 2, pp. 7-16.
Bart, J.C.J., Vavallaro, S.; Gucciardi, E., "Biolubricants: Science and Technology", Woodhead Publishing Limited, Cambridge 2012, pp. 1-6.

* cited by examiner

*Primary Examiner* — Taiwo Oladapo
(74) *Attorney, Agent, or Firm* — Hogan Lovells US LLP

(57) ABSTRACT

Disclosed is a method for production of a methyl ester based formulation. The method involves: providing a feedstock containing about 1% to about 100% canola oil; removing water from the feedstock; heating the feedstock to at least about 60° C.; mixing a solution of about 90% to about 100% (v/v) methanol and a strong base with the heated feedstock to produce a mixture containing methyl ester; and allowing the mixture containing methyl ester to rest for at least one hour. The composition of the methanol and strong base solution being calculated based on the free fatty acid content of the feedstock. The methyl ester based formulations produced by the method can be used as ecofriendly penetrating oils, lubricating oils, machining fluid or releasing agents.

11 Claims, No Drawings

METHODS FOR PRODUCTION OF BIO-BASED LUBRICANTS AND RELATED FLUIDS

CROSS REFERENCE TO RELATED APPLICATIONS

This application claims priority under 35 U.S.C. § 119 to Canada patent application no. 2,904,710, filed Sep. 16, 2015, the entire disclosure of which is incorporated herein by reference.

FIELD OF THE INVENTION

The present invention relates to methods for production of bio-based lubricants and related fluids and more specifically to methods for production of methyl ester based lubricants and related fluids. The related methods involve green technology that result in lubricants and related fluids that are non-toxic, environmentally friendly and are made from renewable sources.

BACKGROUND

Recent concerns with increasing oil prices and sustainability of fossil fuel are creating demand for alternatives to petroleum-based products. Currently, there are industry-wide efforts to replace conventional petroleum-based feedstock with non-petroleum based resources in some sectors. Additionally, public awareness of environmental issues has risen considerably and there is a resolution to ensure that manufacturing methods and products are not endangering the environment. As such, numerous policies and regulations have been put into place, requiring manufactures to follow strict guidelines. In order to overcome the deficiencies of petroleum-based products, many efforts today focus on green technologies. One major area of research is plant biotechnology which offers the solution of producing products that are renewable and environmentally friendly (Bart, 2012).

Despite the rise in green technologies, most lubricants today are typically prepared from petroleum sources. In fact, a majority of general industrial oils, engine oils, transmission and hydraulic fluids, gear oil and greases originate from fossil fuels. Furthermore, the safety and long term exposure effects of these types of lubricants is concerning. Many studies have indicated that petroleum-based lubricants have toxic effects on mammals, fish and bacteria (Bart, 2012). A large proportion of oils are also being released into the environment, for example, from engines, wheel flanges of railway cars and new tires that required mould release agents. Evaporation, spillage and accidents can also pollute the environment with oil. Today's market demands lubricants that are safer to use, made from renewable sources and have superior performance (Bart, 2012). Given the fact that most lubricants are prepared from petroleum sources, the performance and quality of bio-based lubricants may be lagging.

It is therefore necessary to develop processes which can produce bio-based lubricants and related fluids from renewable sources that are non-toxic, environmentally friendly and which may match or surpass the performance of current petroleum-based lubricants and related fluids.

SUMMARY OF THE INVENTION

According to an aspect of the present invention, there is provided a method for production of a methyl ester based formulation. The method comprising the steps of: providing a feedstock comprising about 1% to about 100% canola oil; removing water from the feedstock; heating the feedstock to at least about 60° C.; mixing a solution of about 90% to about 100% (v/v) methanol and a strong base with the heated feedstock to produce a mixture comprising methyl ester, whereby the composition of the solution is calculated based on the free fatty acid content of the feedstock; and allowing the mixture comprising methyl ester to rest for at least one hour.

In one embodiment, the feedstock is vegetable oil, which is either new or used.

In another embodiment, the vegetable oil is filtered to remove solid particulate matter prior to or simultaneously with the step of removing the water from the feedstock.

In a further embodiment, the strong base is potassium hydroxide or sodium hydroxide.

In a still further embodiment, the solution of about 90% to about 100% (v/v) methanol purity and the strong base are mixed with the heated feedstock for at least about two hours.

In yet another embodiment, the method further comprises a step of separating off a glycerine layer from the mixture comprising methyl ester.

In a further embodiment, the method comprises a step of washing the mixture comprising methyl ester to remove particulate matter therefrom. In some cases, the mixture comprising methyl ester is washed with water and is washed until the soap content thereof is less than or equal to 1000 ppm, preferably less than or equal to 50 ppm.

In another embodiment, the method further comprises a step of adding about 1% to about 40% (v/v) of an alcohol, ketone, citric oil and/or emulsifier to the mixture comprising methyl ester. In some exemplary embodiments, the alcohol is methanol and the ketone is acetone. In some cases, about 1% to about 25% (v/v) methanol is added to the mixture comprising methyl ester.

In still another embodiment, the methyl ester based formulation is a penetrating oil, lubricating oil, machining fluid, or release agent for use on concrete or asphalt.

In a further embodiment, the glycerine is used as a dust suppression product or an industrial degreaser.

According to further aspects of the invention, there is a penetrating oil, lubricating oil, machining fluid, dust suppression product, releasing agent an industrial degreaser produced by the method described above.

In one embodiment, the penetrating oil comprises about 1% to about 40% (v/v) methanol or acetone, and, optionally, about 1% to about 40% (v/v) citric oil.

In another embodiment, the lubricating oil comprises less than or equal to 1000 ppm soap content and about 0% to about 25% (v/v) methanol, and, optionally, about 0% to about 40% (v/v) citric oil. The lubricating oil can be formulated, for example, for use as a gun lubricating oil; or chain and cable lubricating oil.

In a further embodiment, the releasing agent comprises about 1% to about 40% emulsifier. The releasing agent can be formulated, for example, for use on concrete or asphalt.

DETAILED DESCRIPTION

Described herein are embodiments of methods for the production of bio-based lubricants and related fluids, in particular methyl ester based formulations. It will be appreciated that the methods, embodiments and examples described herein are for illustrative purposes intended for those skilled in the art and are not meant to be limiting in any way. All references to embodiments or examples throughout the disclosure should be considered a reference to an illustrative and non-limiting embodiment of an illustrative and non-limiting example.

The method for production of a bio-based lubricant and related fluids generally involves: providing a canola oil-based feedstock: removing water from the feedstock; heating the feedstock; mixing a solution of methanol and a strong base with the heated feedstock to produce a mixture comprising methyl ester; and allowing the mixture to rest. The composition of the solution of methanol and the strong base being calculated based on the free fatty acid content of the feedstock. The canola oil-based feedstock preferably contains between about 1% and about 100% canola oil. In addition, approximately 90% to about 100% (v/v) methanol is used in the solution.

The transformation contemplated in this embodiment is transesterification. Transesterification is the method of exchanging the organic group R of an ester with the organic group R' of an alcohol presented in Scheme 1.

Scheme 1 Transesterification

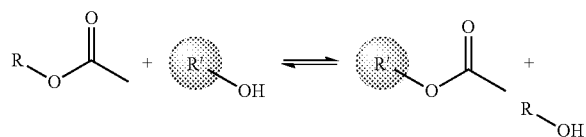

In the context of the present invention, transesterification involves the conversion of triglycerides, diglycerides and monoglycerides in the feedstock into methyl esters and glycerine in the presence of methanol and a strong base. As an example, Scheme 2 depicts the conversion of a triglyceride to three methyl esters and glycerine. This is the main reaction used in the production of biodiesel.

Scheme 2 Transformation of triglycerides to methyl esters

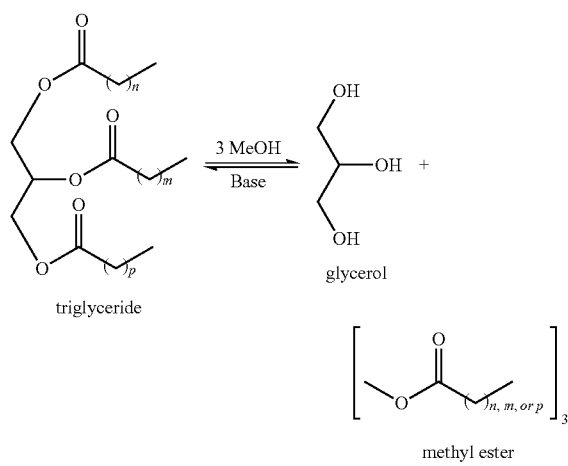

As mentioned above, water may be removed from the feedstock prior to heating the canola oil-based feedstock and performing the reaction with methanol and a strong base. Large quantities of water may increase saponificiation resulting in the production of carboxylate salts. These fatty acid carboxylates can form gels due to their surfactant-like properties, resulting in a mixture that is very difficult to stir. Therefore, the presence of water ultimately results in a reduced amount of methyl ester production. In order to determine if water is still present in the feedstock, a water content test may be performed. One example of the test involves heating a metal surface (for example a saucepan) to approximately 135° C. and applying a sample of oil to the heated surface. If a crackle sound is heard or many small bubbles (vaporized water) emerge, the oil most likely contains water. Water may be removed from the feedstock using any method known to a person skilled in the art, for example, extraction, heating and dehydration. Extraction involves transferring the feedstock to a settling tank for a length of time, for example, 24 hours to a couple of weeks, and draining the water that collects at the bottom. Variations of this method include heating the feedstock to, for example, about 60° C. prior to transferring to a settling tank. Heating involves increasing the temperature of the feedstock to, for example 100° C., to allow the water to evaporate. Lowering the pressure of the system in addition to heating may improve outcomes. Also, drying agents such as $MgSO_4$ or $Na_2SO_4$, or DW10 Ionic exchange resin to dehydrate the oil may also be contemplated. It will be appreciated that a small amount of water may remain in the feedstock as the removal of trace water may prove difficult. However, a small amount of water may not negatively affect the reaction.

The free fatty acid (FFA) content of the feedstock may first be determined to calculate the amount of additional base that is necessary to neutralize the FFAs in the feedstock. Neutralized FFA are expected to separate out of the mixture comprising methyl ester and combine with the glycerine phase (Sarin, 2012). If the FFAs are not neutralized, they may interfere with the transesterification method and the further purification of the mixture comprising methyl ester. It will be understood by a person skilled in the art that FFAs may not be converted to methyl esters in the processes of the present invention without the aid of a carboxylic acid activator and therefore should be neutralized. Typically, new, refined oil contains less than 0.1% FFAs. However, used oil, depending on how long it was used and to what temperatures it was heated, may contain a much higher amount of FFAs. In one example, the FFA content may be determined by titration. An exemplary titration consists of the preparation of a 0.1% w/v solution of base in distilled water. The feedstock, for example 1 mL, is dissolved in, for example, 10 mL of pure isopropanol. For the feedstock to dissolve in the isopropanol, it may be necessary to warm and agitate the mixture until it dissolves and becomes clear. An indicator, for example, a phenolphthalein solution, is added to the mixture. Phenolphthalein remains colourless in solution until the solution reaches a pH of 8.2 or higher (pH of 8.2 to 12.0). The base solution is added slowly to the feedstock solution until a colour change is visible indicating that all the FFAs have been converted to carboxylates by the base and now the excess base is increasing the pH of the solution. The FFA content may be derived from the amount of base used in the titration.

In an embodiment, the total amount of base will include the amount of base for the transesterification of the triglycerides and the amount of base for the neutralization of the FFAs. In one example, every litre of fresh, neat vegetable oil requires about 3 to 7 g of base for transesterification. Therefore, used vegetable oil will require 3 to 7 g of base per liter in addition to the amount of base derived from the titration.

In one example of a method for production of a methyl ester based formulation, the base and methanol may be mixed together prior to addition to the heated feedstock. Generally, the amount of methanol mixture needed is about 20% w/w of the feedstock. However, a person skilled in the art would understand that this ratio may be modified depending on the characteristics of the feedstock, for example, the viscosity of the feedstock. In addition, the present invention contemplates the use of about 90% to 100% (v/v) methanol, for example, but not limited to about 90, 92, 94, 96, 98 or 100% (v/v) methanol. The minimization of the water content in the methanol may result in higher yields of methyl ester formation. One example may involve the use of about 98-100% (v/v) methanol.

It is further contemplated that the method for production of a methyl ester based formulation involves the step of allowing the mixture comprising methyl ester to rest for at least one hour. This settling may allow for the separation of a glycerine layer which can be easily removed. Settling for longer periods of time may improve the separation of the glycerine from the mixture comprising methyl ester.

In one embodiment of a method for production of a methyl ester based formulation, the feedstock is vegetable oil. Vegetable oil encompasses oil extracted from a plant and includes, without being limiting, soybean oil, canola oil, rapeseed oil, sunflower oil, corn oil (maize oil), safflower oil, palm oil, palm kernel oil, peanut oil, flaxseed oil (linseed oil), cottonseed oil, coconut oil, olive oil, grape seed oil, sesame oil, rice bran oil, avocado oil, hemp oil, pumpkin seed oil, tea seed oil, mustard oil, almond oil, macadamia nut oil, hazelnut oil, pine nut oil, pistachio oil, and walnut oil. Vegetable oil may refer to an individual oil derived from the same plant or a blend of several vegetable oils, for example containing canola oil or soybean oil as a major component. It can be appreciated that vegetable oils comprise various lengths of fatty acids which may be saturated, monounsaturated or polyunsaturated. In one embodiment, the feedstock vegetable oil may comprise from about 0 to about 100% canola oil.

The present invention contemplates the use of new or used vegetable oil. Used vegetable oil may be derived from high temperature cooking, for example, deep frying. Common deep frying oils include, without being limiting, soybean oil, canola oil, peanut oil, vegetable oil (a blend) and sunflower oil. It is particularly efficient to utilize used oil from cooking as this oil would otherwise be considered waste and disposed of, for example, in a land-fill. Furthermore, utilizing used vegetable oil in the present invention decreases the cost of the feedstock since low-grade oil may be utilized.

In one example of the present invention, the vegetable oil is filtered to remove solid particulate matter prior to the step of removing the water from the feedstock. It is generally important to remove solid particulate matter so as to prevent equipment damage if the resulting methyl ester based formulation is used on equipment such as injectors, pumps, pistons or seals. In particular, used vegetable oil from deep-fryers may contain numerous solid particulate matter. The particles may be filtered off with a course filter, for example a 400-600 μm filter, and the filter size may be decreased to, for example, 100 μm. The filters may be in the form of strainers or filter bags and the feedstock may be filtered under pressure or under gravity. The solid particulate matter may also be removed from the vegetable oil simultaneously with the step of removing water. For example, the particulate matter may be removed along with the water that has settled at the bottom of a settling tank.

In one embodiment of the method, the strong base that is mixed with methanol and mixed with the heated feedstock is potassium hydroxide or sodium hydroxide. Typically, potassium hydroxide dissolves more quickly in methanol but is more expensive than sodium hydroxide. The final choice of base to be used will depend on the application.

In one embodiment of the method, the solution of about 90% to about 100% (v/v) methanol purity and the strong base are mixed with the heated feedstock for at least about two hours. Longer reaction times may furnish a high yield of the methyl esters. However, prolonged heating may increase side reactions, such as oxidation, and may result in lower yields.

In a further embodiment, the method of the present invention may include the step of separating a glycerine layer from the mixture comprising methyl ester. The glycerine produced from the transesterification, being of higher density, will therefore separate from the mixture comprising methyl ester. The glycerine layer may be removed by decanting the top methyl ester layer. Alternatively, if the mixture is resting in a conical container, the glycerine layer may be drawn off from the bottom.

In yet another embodiment of the method, a further step of washing the mixture comprising methyl ester to remove particulate matter is contemplated. In the context of this step, particulate matter generally refers to soaps (carboxylate salts of FFA, for example sodium or potassium carboxylate salts of FFA), glycerine, excess methanol, diglycerides and monoglycerides. The particulate matter should be removed in order to produce high-quality methyl ester based formulations. The particulate matter may be removed by washing the mixture comprising methyl ester with water. The washing may be performed by any process known in the art, for example, bubble washing, mist washing, or stir washing. Stir washing is an effective method of separating particulate matter and involves vigorously mixing water with the mixture comprising methyl ester and allowing the two phases (water phase and methyl ester phase) to separate. The particulate matter may be slightly more soluble in water than in the mixture comprising methyl ester and may dissolve preferentially in the water phase. After the separated water phase is removed, the process can be repeated a number of times such that the mixture comprising methyl ester remains clear after the phase separation following water addition. In one embodiment of the present method, the mixture is washed until the soap content thereof is less or equal to 1000 ppm. In a further embodiment, the mixture is washed until the particulate content thereof is less than or equal to 50 ppm.

In a further embodiment of the present invention, the method further comprises the step of adding about 1% to about 40% (v/v) of an alcohol, ketone, citric oil and/or emulsifier to the mixture comprising methyl ester. Some examples of alcohols contemplated in the present invention are, without being limiting, methanol, ethanol, propanol and isopropanol. Some examples of ketones are, without being limiting, acetone, butanone and pentan-3-one. As used herein, citric oil refers to an oil derived from the rind of an orange fruit. Extracts of citric oil are also contemplated, such as limonene, which may be the major component in citric oil. In the context of the present invention, the emulsifier refers to a fluid which enables the mixing of water- and oil-based fluids. In one embodiment, the alcohol is methanol. In an even further embodiment, about 1% to about 25% (v/v) methanol is added to the mixture comprising methyl ester. In another embodiment, the ketone is acetone.

The present invention contemplates the use of the methyl ester based formulation as a penetrating oil, lubricating oil, machining fluid or release agent. The present formulations are not petroleum based and do not contain the typical carcinogens and toxins that typical petroleum based lubricants possess. Most importantly, the methyl ester based formulation of this embodiment are biodegradable, environmentally friendly, non-toxic, made from renewable sources, produce low odour and may have a citrus aroma. The present formulations also have very high flashpoint rendering the compositions virtually non-flammable in their liquid states.

In the context of the present invention, penetrating oil generally refers to a fluid that has low viscosity and can penetrate the narrow space between two components, for example, between a seized nut and bolt. The formulation can be effective at cleaning (removing rust, grease, water, oils, dirt, gun powder residue, paint, exhaust soot, dirt and most other contaminants), preventing corrosion (for example, of battery terminals and electrical connections), dispersing moisture, general lubrication, loosening seized components, among other uses. A lubricating oil generally refers to a fluid that is used to reduce friction between surfaces in mutual contact (for example, gears and other moving parts) and can also be effective at cleaning (removing rust, grease, water, oils, dirt, gun powder residue, paint, exhaust soot, dirt and most other contaminants), preventing corrosion and preventing the sticking of ice. Machining fluid, also known as a cutting fluid, encompasses fluids that act as a coolant and lubricant for metalworking processes. A release agent refers to fluid that is used to prevent other materials from bonding to a surface and is used in processes such as mould release or die-cast release.

In one embodiment, the release agent is for use on concrete or asphalt wherein the fluid prevents the adhesion of freshly placed concrete to the forming surface such as plywood, steel and aluminum or from the sticking of asphalt to transportation containers, work equipment and tools.

A further embodiment of the present invention contemplates the use of glycerine obtained from the transesterification as a dust suppression product which allows small dust particles to combine and increase in size, reducing their ability to become airborne. This formulation can reduce the amount of dust becoming airborne on, for example, unpaved roads, mine haul roads, mineral stockpiles, quarries, coal, ore and minerals transport and construction sites. It is typically illegal to apply petroleum based dust suppressants in the environment as these suppressants may be washed off roads by rainfall or blown into the air. Contaminated drinking water or contaminated air is strongly undesirable. Fortunately, the present formulation addresses these problems, offering an environmentally friendly, non-toxic and completely bio-degradable dust suppression product.

The glycerine obtained from the process can also be used as an industrial degreaser that has the same environmental impact as the dust suppression product described above.

The present invention provides a penetrating oil produced from methods comprising adding about 1% to about 40% (v/v) of an alcohol, ketone, citric oil and/or emulsifier to the mixture comprising methyl ester. In one embodiment of the present invention, the penetrating oil comprises about 1% to about 40% (v/v) methanol. In a further embodiment, the penetrating oil comprises about 1% to about 40% (v/v) acetone. In yet a further embodiment, the penetrating oil comprises about 1% to about 40% (v/v) citric oil.

The present invention also provides a lubricating oil produced from methods comprising adding about 1% to about 40% (v/v) of an alcohol, ketone, citric oil and/or emulsifier to the mixture comprising methyl ester. In one embodiment, the alcohol is methanol. In a further embodiment, the lubricating oil comprises about 1% to about 25% (v/v) methanol. In an even further embodiment, the lubricating oil comprises less than or equal to 1000 ppm soap content. In yet a further embodiment, the lubricating oil comprises about 0% to about 40% (v/v) citric oil.

The lubricating oils are contemplated for the use a gun and chain lubricating oils.

It is contemplated that a machining fluid is produced by washing the methyl ester mixture until the particulate content is less than or equal to 50 ppm.

It is also contemplated that a dust suppression oil product is produced by separating the glycerine layer from the mixture comprising the methyl ester.

It is contemplated that a releasing agent is produced by adding about 1% to about 40% (v/v) of an alcohol, ketone, citric oil and/or emulsifier to the mixture comprising methyl ester. In a further embodiment, the releasing agent comprises about 1% to about 40% emulsifier. The releasing agents are contemplated for use on concrete and asphalt.

Exemplary formulations include:

Penetrant

About 1% to about 40% by volume of methanol/acetone to unwashed methyl ester formulation, and, optionally, about 1% to about 40% by volume citric oil to unwashed methyl ester formulation.

Lubricant

Water washed methyl ester formulation having less than 1000 ppm soap content.

Gun Lubricating Oil

About 1% to about 20% by volume of methanol to unwashed methyl ester formulation, and, optionally, about 1% to about 40% by volume citric oil to unwashed methyl ester formulation.

Machining Fluid

Water washed methyl ester formulation having less than 50 ppm soap content.

Chain and Cable Lubricant

About 1% to about 20% by volume of methanol to unwashed methyl ester formulation.

Dust Suppression Oil Product or Industrial Degreaser

Glycerine removed from methyl ester formulation.

Asphalt and Concrete Releasing Agents

Unwashed methyl ester formulation and about 1% to 40% emulsifier.

Various embodiment of methyl ester based formulations and methods for their productions have been described. The above-described embodiments are intended to be examples and alteration and modifications may be effected thereto, by those of ordinary skill in the art, without departing from the scope of the teachings.

REFERENCES

Sarin, A. *Biodiesel: production and properties*. Royal Society of Chemistry: Cambridge, 2012.

Bart, J. C. J.; Cavallaro, S.; Gucciardi, E. *Biolubricants: Science and technology*. Woodhead Publishing Limited: Cambridge, 2012.

We claim:

1. A method for production of a methyl ester based formulation, the method comprising the steps of:
    (A) providing a feedstock comprising about 1% to about 100% canola oil, if the feedstock contains water, removing water from the feedstock;
    (B) heating the feedstock to at least about 60° C.;
    (C) adding a strong base and a solution of about 90% to about 100% (v/v) methanol to the heated feedstock to produce a mixture comprising methyl ester;

(D) allowing the mixture comprising methyl ester to settle for at least one hour, and separating a glycerine layer from the mixture comprising methyl ester; and
(E) then adding about 1% (v/v) methanol or acetone and 1% to 40% (v/v) citric oil to the mixture comprising methyl ester to form the methyl ester based formulation.

2. The method of claim 1, wherein the strong base is potassium hydroxide or sodium hydroxide.

3. The method of claim 1, wherein the solution of a strong base and about 90% to about 100% (v/v) methanol is added to the heated feedstock and then mixed for at least about two hours.

4. The method of claim 1, further comprising a step of washing the mixture comprising methyl ester to remove particulate matter therefrom.

5. The method of claim 4, wherein the mixture comprising methyl ester is washed with water.

6. The method of claim 5, wherein the mixture comprising methyl ester is washed until the soap content thereof is less than or equal to 1000 ppm.

7. The method of claim 5, wherein the mixture comprising methyl ester is washed until the particulate content thereof is less than or equal to 50 ppm.

8. The method of claim 1, further comprising the step of adding about 1% to about 40% (v/v) of an emulsifier to the mixture comprising methyl ester.

9. The method of claim 1, wherein the methyl ester based formulation is a penetrating oil, lubricating oil, machining fluid, industrial degreaser or release agent.

10. The method of claim 9, wherein the release agent is for use on concrete or asphalt or ice.

11. The method of claim 1, wherein the glycerine is used as a dust suppression product or an industrial degreaser.

* * * * *